United States Patent [19]
Crowell et al.

[11] Patent Number: 5,958,917
[45] Date of Patent: Sep. 28, 1999

[54] BENZOFLUORENE COMPOUNDS, INTERMEDIATES, COMPOSITIONS, AND METHODS

[75] Inventors: Thomas Alan Crowell; Charles David Jones; Henry Uhlman Bryant, all of Indianapolis, Ind.

[73] Assignee: Eli Lilly and Company, Indianapolis, Ind.

[21] Appl. No.: 08/936,671

[22] Filed: Sep. 24, 1997

Related U.S. Application Data

[60] Provisional application No. 60/026,750, Sep. 26, 1996.
[51] Int. Cl.$^6$ ...................... C07D 211/31; C07D 211/00; A61K 31/445
[52] U.S. Cl. .................. 514/212; 514/239.2; 514/319; 514/428; 540/609; 544/173; 546/195; 548/528
[58] Field of Search ................ 514/212, 239.2, 514/319, 428; 540/609; 544/173; 546/195; 548/528

[56] References Cited

U.S. PATENT DOCUMENTS

| | | | |
|---|---|---|---|
| 3,394,125 | 7/1968 | Crenshaw | 260/326.5 |
| 3,413,305 | 11/1968 | Crenshaw | 260/326.5 |
| 4,133,814 | 1/1979 | Jones et al. | 260/326 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 5,147,880 | 9/1992 | Jones | 514/319 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/233.5 |

FOREIGN PATENT DOCUMENTS

| | | |
|---|---|---|
| 062 503 | 10/1982 | European Pat. Off. . |
| WO 89/02893 | 4/1989 | WIPO . |
| WO 95/10513 | 4/1995 | WIPO . |

OTHER PUBLICATIONS

Jones, C.D., et al, *J. Med. Chem.* 35: 931–938, 1992.
Crenshaw, R.R., et al, *J. Med. Chem.* 14(12):1185–1190 (1971).
Jones, C.D., et al, *J. Med. Chem.* 27: 1057–1066) 1984.

*Primary Examiner*—Richard L. Raymond
*Assistant Examiner*—Deepak R. Rao
*Attorney, Agent, or Firm*—Gilbert T. Voy

[57] ABSTRACT

The present invention provides compounds of formula I

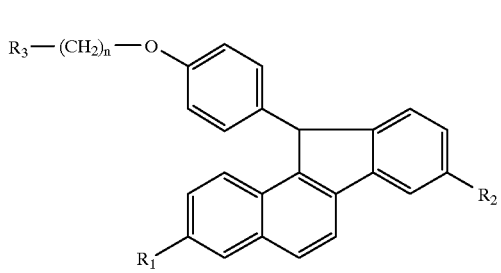

wherein $R_1$ is —H, —OH, —O($C_1$–$C_4$ alkyl), —OCO($C_1$–$C_6$ alkyl), —OCOO($C_1$–$C_6$ alkyl), —OCOAr, —OCOOAr, or —OSO$_2$($C_2$–$C_6$ alkyl);

$R_2$ is —OH, —O($C_1$–$C_4$ alkyl), —OCO($C_1$–$C_6$ alkyl), —OCOO($C_1$–$C_6$ alkyl), —OCOAr, —OCOOAr, or —OSO$_2$($C_2$–$C_6$ alkyl);

$R_3$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino; and n is 2 or 3;

or a pharmaceutically acceptable salt or solvate thereof.

11 Claims, No Drawings

BENZOFLUORENE COMPOUNDS, INTERMEDIATES, COMPOSITIONS, AND METHODS

This application claims the benefit of U.S. Provisional Application No. 60/026,750 filed Sep. 26, 1996.

BACKGROUND OF INVENTION

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

The instant invention provides benzofluorene compounds, pharmaceutical formulations thereof, and methods of using such compounds at least, for example, in the inhibition, treatment, or prevention of the disease states as indicated herein.

SUMMARY OF THE INVENTION

The present invention relates to compounds of formula I

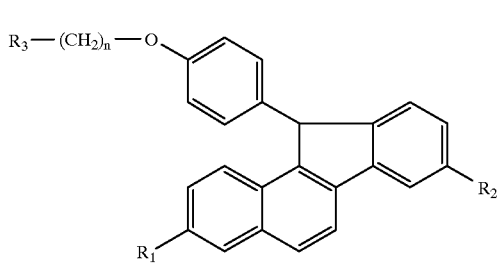

wherein $R_1$ is —H, —OH, —O($C_1$–$C_4$ alkyl), —OCO($C_1$–$C_6$ alkyl) —O(CO)O($C_1$–$C_6$ alkyl), —OCOAr, —O(CO)OAr, where Ar is phenyl or optionally substituted phenyl, or —OSO$_2$($C_2$–$C_6$ alkyl);

$R_2$ is —OH, —O($C_1$–$C_4$ alkyl), —OCO($C_1$–$C_6$ alkyl), —O(CO)O($C_1$–$C_6$ alkyl), —OCOAr, —O(CO)OAr, where Ar is phenyl or optionally substituted phenyl, or —OSO$_2$($C_2$–$C_6$ alkyl);

$R_3$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino; and n is 2 or 3;

or a pharmaceutically acceptable salt or solvate thereof.

The instant invention further provides pharmaceutical formulations containing compounds of formula I, and the use of said compounds at least for the inhibition of bone loss or bone resorption, particularly osteoporosis, cardiovascular-related pathological conditions, including hyperlipidemia, and estrogen-dependent cancer.

The present invention also relates to intermediate compounds of formula II which are useful for preparing the pharmaceutically active compounds of the present invention:

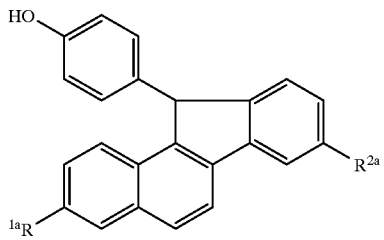

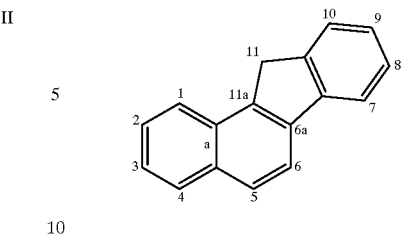

wherein:

R$^{1a}$ is —H or —OR$^5$ in which R$^5$ is a hydroxy protecting group.

R$^{2a}$ is —OR$^6$ in which R$^6$ is a hydroxy protecting group; or a pharmaceutically acceptable salt thereof.

DETAILED DESCRIPTION OF THE INVENTION

General terms used in the description of compounds herein described bear their usual meanings. For example, "$C_1$–$C_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "—OC$_1$–C$_4$ alkyl" represents a $C_1$–$C_4$ alkyl group attached through an oxygen such as, for example, methoxy, ethoxy, n-propoxy, isopropoxy, and the like. Of these $C_1$–$C_4$ alkoxy groups, methoxy is highly preferred The term "substituted phenyl" refers to a phenyl group having one or more substituents selected from the group consisting of $C_1$–$C_4$ alkyl, —OC$_1$–C$_4$ alkyl, hydroxy, nitro, chloro, fluoro, or tri(chloro or fluoro)methyl.

The term "hydroxy protecting group" contemplates numerous functionalities used in the literature to protect a hydroxyl function during a chemical sequence and which can be removed to yield the phenol. Included within this group would be acyls, mesylates, tosylates, benzyl, alkylsilyloxys, —OC$_1$–C$_4$ alkyls, and the like. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for removing preferred hydroxy protecting groups, particularly methyl and alkylsilyloxy, are essentially as described in the Examples infra.

Optionally substituted phenyl includes phenyl and phenyl substituted once or twice with $C_1$–$C_6$ alkyl, $C_1$–$C_4$ alkoxy, hydroxy, nitro, chloro, fluoro, or tri (chloro or fluoro)methyl.

The term "solvate" represents an aggregate that comprises one or more molecules of the solute, such as a formula I compound, with one or more molecules of solvent.

The term "inhibit" includes its generally accepted meaning which includes prohibiting, preventing, restraining, and slowing, stopping, or reversing progression, severity, or ameliorating a resultant symptom or effect.

Compounds of the present invention are named as derivatives of benzo[a]fluorene in accordance to the Ring Index, The American Chemical Society, as follows:

Compounds of formula I include, but are not limited to:
3,8-dimethoxy-11-[4-[2-(1-piperidinyl)ethoxy]phenyl]-11H-benzo[a]fluorene;
3,8-dihydroxy-11-[4-[2-(1-piperidinyl)ethoxy]phenyl]-11H-benzo[a]fluorene;
3-hydroxy-8-methoxy-11-[4-[2-(1-piperidinyl)ethoxy]phenyl]-11H-benzo[a]fluorene;
3-methoxy-8-hydroxy-11-[4-[2-(1-piperidinyl)ethoxy]phenyl]-11H-benzo[a]fluorene;
3,8,9-trimethoxy-11-[4-[2-(1-piperidinyl)ethoxy]phenyl]-11H-benzo[a]fluorene;
3,8,10-trimethoxy-11-[4-[2-(1-piperidinyl)ethoxy]phenyl]-11H-benzo[a]fluorene;
9-fluoro-3,8-dimethoxy-11-[4-[2-(1-piperidinyl)ethoxy]phenyl]-11H-benzo[a]fluorene;
9-chloro-3,8-dimethoxy-11-[4-[2-(1-piperidinyl)ethoxy]phenyl]-11H-benzo[a]fluorene;
3,8-dimethoxy-9-methyl-11-[4-[2-(1-piperidinyl)ethoxy]phenyl]-11H-benzo[a]fluorene;
3,8-dimethoxy-9-ethyl-11-[4-[2-(1-piperidinyl)ethoxy]phenyl]-11H-benzo[a]fluorene;
8-methoxy-11-[4-[2-(1-piperidinyl)ethoxy]phenyl]-11H-benzo[a]fluorene;
8-hydroxy-11-[4-[2-(1-piperidinyl)ethoxy]phenyl]-11H-benzo[a]fluorene;
8,9-dimethoxy-11-[4-[2-(1-piperidinyl)ethoxy]phenyl]-11H-benzo[a]fluorene;
8,10-dimethoxy-11-[4-[2-(1-piperidinyl)ethoxy]phenyl]-11H-benzo[a]fluorene;
9-fluoro-8-methoxy-11-[4-[2-(1-piperidinyl)ethoxy]phenyl]-11H-benzo[a]fluorene;
9-chloro-8-methoxy-11-[4-[2-(1-piperidinyl)ethoxy]phenyl]-11H-benzo[a]fluorene;
8-methoxy-9-methyl-11-[4-[2-(1-piperidinyl)ethoxy]phenyl]-11H-benzo[a]fluorene;
8-methoxy-9-ethyl-11-[4-[2-(1-piperidinyl)ethoxy]phenyl]-11H-benzo[a]fluorene;
3,8-dimethoxy-11-[4-[2-(1-pyrrolidinyl)ethoxy]phenyl]-11H-benzo[a]fluorene;
3,8-dihydroxy-11-[4-[2-(1-pyrrolidinyl)ethoxy]phenyl]-11H-benzo[a]fluorene;
3-hydroxy-8-methoxy-11-[4-[2-(1-pyrrolidinyl)ethoxy]phenyl]-11H-benzo[a]fluorene;
3-methoxy-8-hydroxy-11-[4-[2-(1-pyrrolidinyl)ethoxy]phenyl]-11H-benzo[a]fluorene;
8-methoxy-11-[4-[2-(1-pyrrolidinyl)ethoxy]phenyl]-11H-benzo[a]fluorene;
8-hydroxy-11-[4-[2-(1-pyrrolidinyl)ethoxy]phenyl]-11H-benzo[a]fluorene;
8,9-dimethoxy-11-[4-[2-(1-pyrrolidinyl)ethoxy]phenyl]-11H-benzo[a]fluorene;
8,10-dimethoxy-11-[4-[2-(1-pyrrolidinyl)ethoxy]phenyl]-11H-benzo[a]fluorene;
3,8-dimethoxy-11-[4-[2-(1-methylpyrrolidinyl)ethoxy]phenyl]-11H-benzo[a]fluorene;
3,8-dihydroxy-11-[4-[2-(1-hexamethyleneimino)ethoxy]phenyl]-11H-benzo[a]fluorene;

3-hydroxy-8-methoxy-11-[4-[2-(1-morpholino)ethoxy] phenyl]-11H-benzo[a]fluorene;
3-methoxy-8-hydroxy-11-[4-[2-(N,N-dimethylamino) ethoxy]phenyl]-11H-benzo[a]fluorene;
3,8,9-trimethoxy-11-[4-[2-(N,N,-diethylamino)ethoxy] phenyl]-11H-benzo[a]fluorene;
3,8,10-trimethoxy-11-[4-[2-(1-methylpyrrolidinyl)ethoxy] phenyl]-11H-benzo[a]fluorene;
9-fluoro-3,8-dimethoxy-11-[4-[2-(N,N-dimethylamino) ethoxy]phenyl]-11H-benzo[a]fluorene;
9-chloro-3,8-dimethoxy-11-[4-[2-(N,N-diisopropylamino) ethoxy]phenyl]-11H-benzo[a]fluorene;
8-methoxy-11-[4-[2-(1-pyrrolidinyl)ethoxy]phenyl]-11H-benzo[a]fluorene;
8-hydroxy-11-[4-[2-(1-methylpyrrolidinyl)ethoxy]phenyl]-11H-benzo[a]fluorene;
8,9-dimethoxy-li-[4-[2-(1-methylpyrrolidinyl)ethoxy] phenyl]-11H-benzo[a]fluorene;
8,10-dimethoxy-11-[4-[2-(1-methylpyrrolidinyl)ethoxy] phenyl]-11H-benzo[a]fluorene; and the like.

The compounds of formula II include, but are not limited to:
4-(3,8-dimethoxy-11H-benzo[a]fluoren-11-yl)phenol;
4-k(3,8,9-trimethoxy-11H-benzo[a]fluoren-11-yl)phenol;
4-(3,8-10-trimethoxy-11H-benzo[a]fluoren-11-yl)phenol;
4-(9-fluoro-3,8-dimethoxy-11H-benzo[a]fluoren-11-yl) phenol;
4-(9-chloro-3,8-dimethoxy-11H-benzo[a]fluoren-11-yl) phenol;
4-(3,8-dimethoxy-9-methyl-11H-benzo[a]fluoren-11-yl) phenol;
4-(3,8-dimethoxy-9-ethyl-11H-benzo[a]fluoren-11-yl) phenol;
4-(8-methoxy-11H-benzo[a]fluoren-11-yl)phenol;
4-(8,9-dimethoxy-11H-benzo[a]fluoren-11-yl)phenol;
4-(8,10-dimethoxy-11H-benzo[a]fluoren-11-yl)phenol;
4-(9-fluoro-8-methoxy-11H-benzo[a]fluoren-11-yl)phenol;
4-(9-chloro-8-methoxy-11H-benzo[a]fluoren-11-yl)phenol;
4-(8-methoxy-9-methyl-11H-benzo[a]fluoren-11-yl)phenol;
4-(8-methoxy-9-ethyl-11H-benzo[a]fluoren-11-yl)phenol;
and the like.

The starting material for preparing compounds of the present invention is a compound of formula III

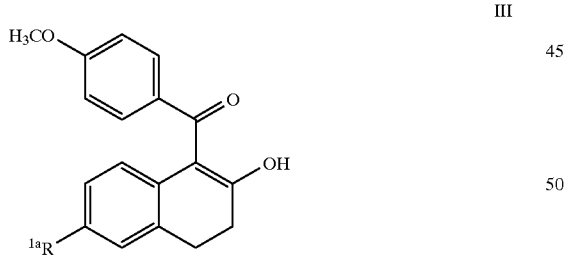

III wherein $R^{1a}$ is —H or —$OR^5$ in which $R^5$ is a hydroxy protecting group.

Compounds of formula III are known in the art and are prepared essentially as described by Jones et al. in U.S. Pat. No. 4,400,543 and Jones, et al., in U.S. Pat. No. 5,147,880 the disclosures of which are herein incorporated by reference. See, also, Jones et al., *J. Med. Chem.*, 35: 931–8 (1992) and Jones et al., *J. Med. Chem.*, 22: 962 (1979).

In preparing compounds of the present invention, generally, a 1-acylated-2-tetralone of formula III is treated with a base to form its corresponding anion, which is reacted with diphenylchlorophosphate, providing an enol phosphate derivative of formula IV. The formula IV compound undergoes formal addition-elimination when treated with an aryl Grignard reagent, which results in substitution of the 2-phosphate substituent by the aryl moiety, thereby producing a compound of formula V. Dealkylation of a formula V compound by a thiolate anion demethylation reagent selectives dealkylates the group which is located para- to the electron-withdrawing carbonyl group. The result of such selective dealkylation is a phenolic compound of formula VI, which can be cyclized under the influence of acid catalysts. Cyclization of an intermediate of formula VI is accompanied by a dehydration process which produces a fully aromatic naphthalene ring in the product of formula II. A compound of formula I serves as an intermediate to the compounds of this invention. This synthetic route is as shown below in Scheme I, and $R^{1a}$ and $R^{2a}$ are as defined above.

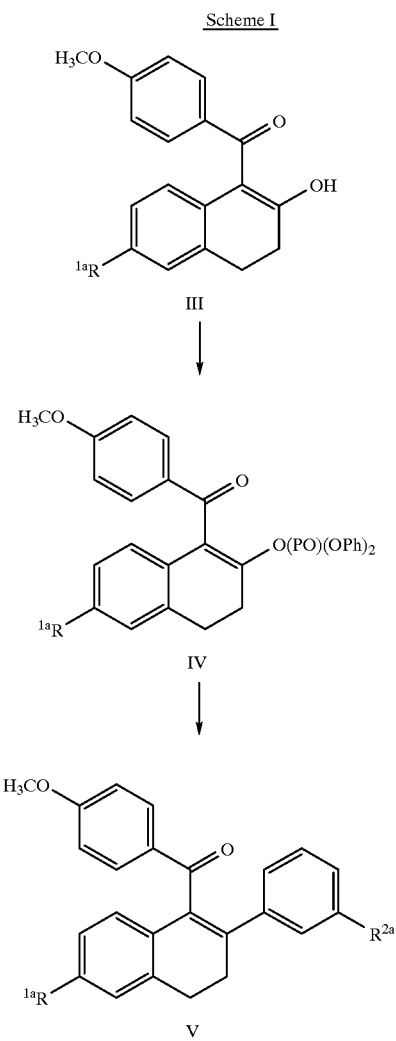

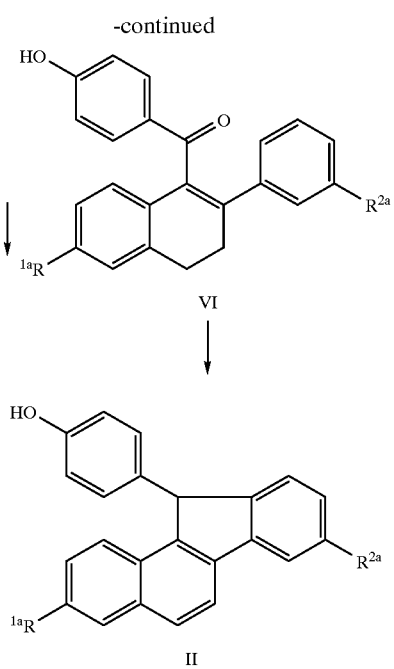

In the first step of this process, a compound of formula III is converted to a dihydronaphthalene derivative of formula II via a two-step protocol, essentially as described by Jones et al., *J. Med. Chem.*, 35: 931–8 (1992). A formula III enolic compound is phosphorylated by one or more equivalents of a phosphorylating reagent which is a diarylchloro- or diarylbromo-phosphate and preferably diphenylchlorophosphate. This reaction may be carried out in a variety of inert solvents including ethers, THF, dioxane, ethyl acetate, toluene, and acetonitrile and in the presence of an acid scavenger such as an alkali metal hydride, alkali metal hydroxide, or alkali metal carbonate or a trialkyl amine such as triethyl amine. The alkali metal base or tertiary amine may also act as a basic catalyst in the phosphorylation process. Although it is preferable to run the reaction at ice bath temperature so as to avoid unwanted side products, elevated temperatures can also be used, but they are usually unnecessary to complete the phosphorylation reaction. The product of the phosphorylation reaction, an enol phosphate derivative of formula IV, may be isolated by usual techniques, such as chromatography. However, it is most convenient to generate the enolphosphate using a solvent/acid scavenger combination which is compatible with the next step of the reaction (addition of a Grignard reagent). Thus, the combination of sodium hydride in THF under a nitrogen atmosphere is preferred, and leads to a rapid phosphorylation leading to a compound of formula IV.

The intermediate enol phosphate, either isolated or generated in situ, may then be reacted with one or more equivalents of an aryl Grignard reagent or an aryl lithium organocuprate reaent. One to two equivalents of an aryl magnesium bromide is preferred, and phenyl magnesium bromide or 4-methoxyphenyl magnesium bromide is particularly preferred. The reaction is typically conducted at ice bath temperature to minimize side reactions, but elevated temperatures can be used to increase the rate of the reaction. The addition of the aryl moiety, followed by the elimination of the phosphate leaving group (formally an addition, elimination process) gives rise to a dihydronaphthalene derivative of formula V, which can be isolated by conventional techniques such as crystallization or chromatography.

The resulting dihydronaphthalene derivative of formula V is then demethylated to provide an intermediate of formula VI. In order to accomplish regioselective demethylation at the methoxy group para to the carbonyl, a nucleophilic demethylation reagent is used, and alkali metal thiolates (alkali metal salt of an organic thiol) are preferred. Especially preferred are lithium thioethylate or lithium thiomethylate, in excess to the extent of 1.2 or more equivalents of the demethylation reagent over the substrate. The reaction is conducted under an inert atmosphere to preserve the demethylation reagent and in a solvent which is practically inert to the nucleophilic nature of the thiolate reagent. Suitable solvents for the demethylation are those which are most conducive to bimolecular nucleophilic displacement reactions, and these include dimethylsulfoxide dimethylformamide, dimethylacetamide, and THF; Anhydrous dimethylformamide is preferred. In order to sumultaneously achieve a satisfactory reaction rate and also obtain good control of the selectivity for demethylation at the site para to the carbonyl group, it is important to carefully control the temperature of the reaction. Although the demethylation process will take place in the range of temperatures from 60° C. to 120° C., it is advantageous to use a temperature in the range of 80–90° C. to optimize the yield of the desired product. A temperature of 80° C. is particularly preferred. Under the preferred reaction conditions, the transformation from a formula VI compound to a formula V compound is complete after heating for about 2 to 4 hours at the indicated temperature.

In the final transformation shown in Scheme I, the dihydronaphthalene derivative of formula VI undergoes a cyclization-dehydration process which produces the benzofluorene derivative of formula II. This process is acid-catalyzed and a variety of mineral acids, Lewis acids, and organic acids may be used. Among these catalysts are alkylsulfonic acids, aryl sulfonic acids, sulfuric acid, hydrochloric acid, hydrobromic acid, polyphosphoric acid, and boron trifluoride etherate. Methane sulfonic acid (neat) and borontrifluoride etherate are preferred, and methane sulfonic acid is particularly so. The reactions typically proceed at room temperature, but higher temperatures may be advantageous in speeding up the reaction rate.

Under the preferred reaction conditions, the transformation from a formula VI compound to a formula II compound is complete after stirring for about 5 minutes to about 3 hours at ambient temperatures.

Compounds of formula II are useful for the preparation of pharmaceutically active compounds of formula I of the present invention.

Upon preparation of a formula II compound, it is reacted with a compound of formula VII

wherein $R^3$ and n are as defined above and Q is a bromo or, preferably, a chloro moiety, to form a compound of formula Ia. The formula Ia compound is then deprotected, when $R^5$ and/or $R^6$ hydroxy protecting groups are present, to form a compound of formula Ib. These process steps are shown in Scheme II below.

Scheme II

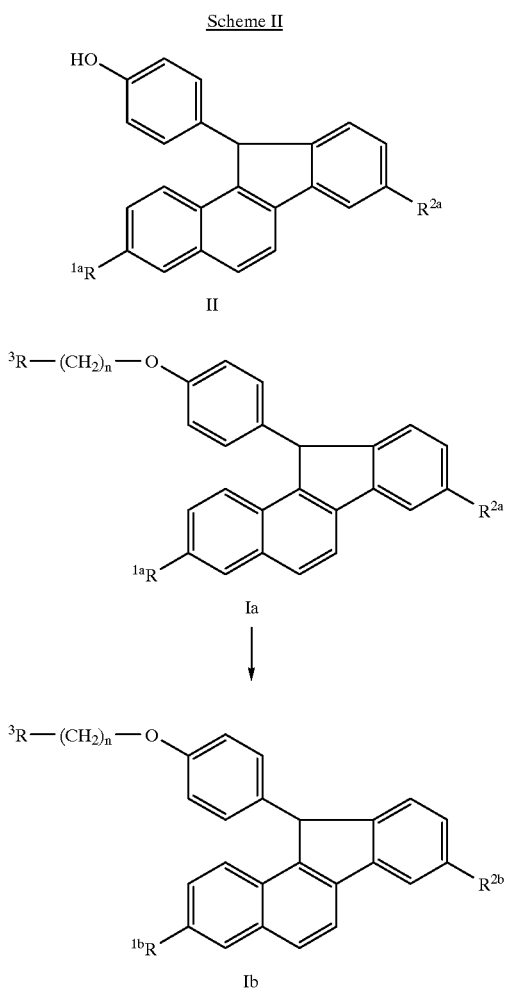

wherein:

$R^{1a}$, $R^{2a}$, $R^3$, and n are as defined above;
$R^{1b}$ is —H or —OH; and
$R^{2b}$ is —OH;
or a pharmaceutically acceptable salt or solvate thereof.

In the first step of the process shown in Scheme II, the alkylation is carried out via standard procedures. Compounds of formula VII are commercially available or are prepared by means well known to one of ordinary skill in the art. Preferably, the hydrochloride salt of a formula VII compound, particularly 2-chloroethylpiperidine hydrochloride, is used.

Generally, at least about 1 equivalent of formula II substrate are reacted with 2 equivalents of a formula VII compound in the presence of at least about 4 equivalents of an alkali metal carbonate, preferably cesium carbonate or potassium carbonate, and an appropriate solvent.

Solvents for this reaction are those solvents or mixture of solvents which remain inert throughout the reaction. N,N-dimethylformamide, especially the anhydrous form thereof, is preferred.

The temperature employed in this step should be sufficient to effect completion of this alkylation reaction. Often, ambient temperature is sufficient and preferred, but in certain cases, higher temperatures may be required.

The present reaction preferably is run under an inert atmosphere, particularly nitrogen.

Under the preferred reaction conditions, this reaction will run to completion in about 16 to about 20 hours. Of course, the progress of the reaction can be monitored via standard chromatographic techniques.

As an alternative for preparing compounds of formula Ia, a formula II compound is reacted with an excess of an alkylating agent of the formula

wherein Q and Q' each are the same or different leaving group, in an alkali solution. Appropriate leaving groups include the sulfonates such as methanesulfonate, 4-bromobenzenesulfonate, toluenesulfonate, ethanesulfonate, isopropylsulfonate, 4-methoxybenzenesulfonate, 4-nitrobenzenesulfonate, 2-chlorobenzenesulfonate, triflate, and the like, halogens such as bromo, chloro, and iodo, and other related leaving groups. Halogens are preferred leaving groups and bromo is especially preferred.

A preferred alkali solution for this alkylation reaction contains potassium carbonate in an inert solvent such as, for example, methyethyl ketone (MEK) or DMF. In this solution, the 4-hydroxy group of the phenolic moiety of a formula II compound exists as a phenoxide ion which displaces one of the leaving groups of the alkylating agent.

This reaction is best when the alkali solution containing the reactants and reagents is brought to reflux and allowed to run to completion. When using MEK as the preferred solvent, reaction times run from about 6 hours to about 20 hours.

The reaction product from this step is then reacted with 1-piperidine, 1-pyrrolidine, methyl-1-pyrrolidine, dimethyl-1-pyrrolidine, 4-morpholine, dimethylamine, diethylamine, or 1-hexamethyleneimine, or other secondary amines, via standard techniques, to form compounds of formula Ia. Preferably, the hydrochloride salt of piperidine is reacted with the alkylated compound of formula IIb in an inert solvent, such as anhydrous DMF, and heated to a temperature in the range from about 60° C. to about 110° C. When the mixture is heated to a preferred temperature of about 90° C., the reaction only takes about 30 minutes to about 1 hour. However, changes in the reaction conditions will influence the amount of time this reaction needs to be run to completion. Of course, the progress of this reaction step can be monitored via standard chromatographic techniques.

An alternative route for preparing compounds of the present invention is depicted in Scheme III, in which $R^{1a}$, $R^{2a}$ and $R^3$ are as defined above.

Scheme III

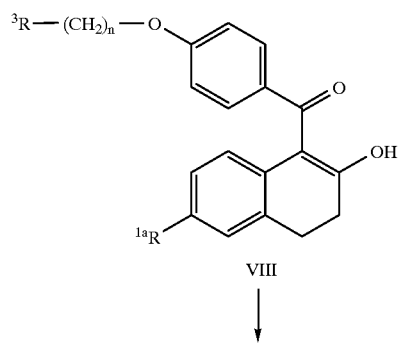

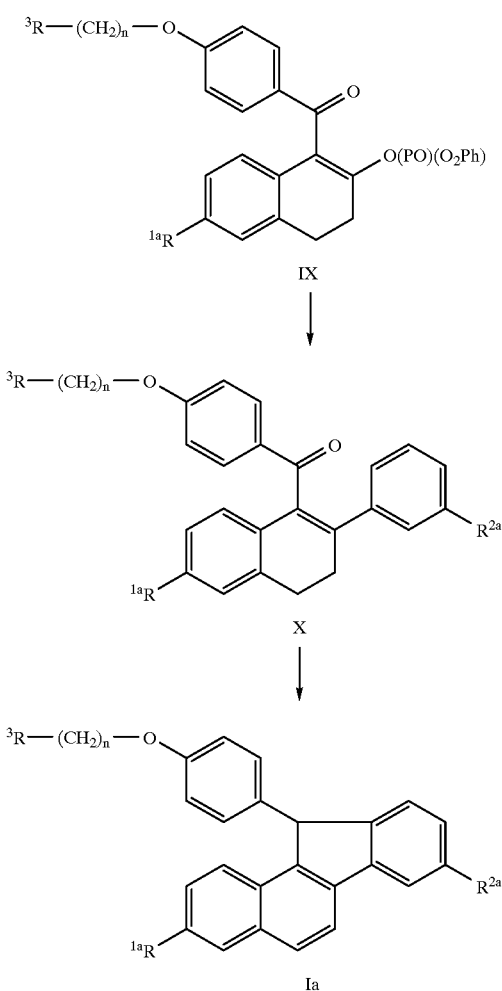

In this alternative, the starting material, a 1-acylated-2-tetralone of formula VIII already includes the basic side chain moiety. The compound of formula VIII treated with a base to form its corresponding anion, which is reacted with diphenylchlorophosphate, providing an enol phosphate derivative of formula IX. The formula IX compound undergoes formal addition-elimination when treated with an aryl Grignard reagent, which results in substitution of the 2-phosphate substituent by the aryl moiety, thereby producing a dihydronaphthalene compound of formula X. The compound of formula X can be cyclized under acidic conditions to a formula Ia compound of this invention A formula VIII enolic compound which already bears the basic side chain is phosphorylated by one or more equivalents of a phosphorylating reagent which is a diarylchloro- or diarylbromo-phosphate and preferably diphenylchlorophosphate. This reaction, may be carried out in a variety of inert solvents including ethers, THF, dioxane, ethyl acetate, toluene, and acetonitrile and in the presence of an acid scavenger such as an alkali metal hydride, alkali metal hydroxide, or alkali metal carbonate or a trialkyl amine such as triethyl amine. The alkali metal base or tertiary amine may also act as a basic catalyst in the phosphorylation process. Although it is preferable to run the reaction at ice bath temperature so as to avoid unwanted side products, elevated temperatures can also be used, but they are usually unnecessary to complete the phosphorylation reaction The product of the phosphorylation reaction, an enol phosphate derivative of formula IX may be isolated by usual techniques, such as chromatography. However, it is most convenient to generate the enolphosphate using a solvent/acid scavenger combination which is comparable with the next step of the reaction (additon of a Grignard Reagent). Thus, the combination of sodium hydride in THF under a nitrogen atmosphere is preferred, and leads to a rapid phosphorylation leading to a compound of formula IX.

The intermediate enol phosphate of formula IX is either isolated or generated in situ, and is then reacted with one or more equivalents of an aryl Grignard reagent or an aryl lithium organocuprate reagent. One to two equivalents of an aryl magnesium bromide is preferred, and phenyl magnesium bromide or 4-methoxyphenyl magnesium bromide is particularly preferred. The reaction is typically conducted at ice bath temperature to minimize side reactions, but elevated temperatures can be used to increase the rate of the reaction. The addition of the aryl moiety, followed by the elimination of the phosphate leaving group (formally an addition, elimination process) gives rise directly to a dihydronaphthalene derivative of formula X, which can be isolated by conventional techniques such as crystallization of the free base or salts or chromatography of the former.

In the final transformation shown in Scheme III, the dihydronaphthalene derivative of formula X undergoes a cyclization-dehydration process which produces the benzofluorene derivative of formula Ia. This process is acid-catalyzed and a variety of mineral acids, Lewis acids, and organic acids may be used. Among these catalysts are alkylsulfonic acids, aryl sulfonic acids, sulfuric acid, hydrochloric acid, hydrobromic acid, polyphosphoric acid, and boron trifluoride etherate. Methane sulfonic acid (neat) and borontrifluoride etherate are preferred, and methane sulfonic acid is particularly so. The reactions typically proceed at room temperature, but higher temperatures may be advantageous in speeding up the reaction rate.

Under the preferred reaction conditions, the transformation from a formula X compound to a formula IIa compound is complete after stirring for about 5 minutes to about 3 hours at ambient temperatures.

Compounds of formula Ia, in which $R^5$ and/or $R^6$, when present, are $C_1$–$C_4$ alkyl, preferably methyl, are pharmaceutically active for the methods herein described. Accordingly, such compounds are encompassed by the definition herein of compounds of formula I.

Preferred compounds of formula I are obtained by cleaving, when present, the $R^5$ and $R^6$ hydroxy protecting groups of formula Ia compounds via well known procedures. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for removing preferred $R^5$ and/or $R^6$ hydroxy protecting groups, particularly methyl, are essentially as described in the Examples, infra.

Other preferred compounds of formula I are prepared by replacing the 3 and/or 8-position hydroxy moieties, when present, with a moiety of the formula —O—CO—($C_1$–$C_6$ alkyl), or —O—$SO_2$—($C_2$–$C_6$ alkyl) via well known procedures. See, for example, U.S. Pat. No. 4,358,593, the disclosure of which is herein incorporated by reference.

For example, when an —O—CO($C_1$–$C_6$ alkyl) group is desired, a mono- or dihydroxy compound of formula I is reacted with an acylating agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, for example, Haslam et al., *Tetrahedron*, 36:2409–2433 (1980).

The present reactions are carried out at moderate temperatures, in the range from about −25° C. to about 100° C., frequently under an inert atmosphere such as nitrogen gas. However, ambient temperature is usually adequate for the reaction to run.

Acylation of a 3-position and/or 8-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

The aforementioned $R^1$ and/or $R^2$ groups of formula I compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, for example, *Bull. Chem. Soc. Japan*, 38:1979 (1965), and *Chem. Ber.*, 788 and 2024 (1970).

Each of the above techniques which provide —O—CO—($C_1$–$C_6$ alkyl) moieties are carried out in solvents as discussed above. Those techniques which do not produce an acid product in the course of the reaction, of course, do not call for the use of an acid scavenger in the reaction mixture.

When a formula I compound is desired in which the 3-and/or 8-position hydroxy group of a formula I compound is converted to a group of the formula —O—$SO_2$—($C_2$–$C_6$ alkyl), the mono- or dihydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). The dihydroxy compound also can be reacted with the appropriate sulfonic anhydride or mixed sulfonic anhydrides. Such reactions are carried out under conditions such as were explained above in the discussion of reaction with acid halides and the like.

Although the free-base form of formula I compounds can be used in the methods of the present invention, it is preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The instant invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the instant invention which is capable of inhibiting, alleviating, ameliorating, treating, or preventing further symptoms in mammals, including humans, suffering from bone loss or bone resorption, particularly osteoporosis, and cardiovascular-related pathological conditions including hyperlipidemia, and other cardiovascular pathologies.

In the case of estrogen-dependent cancers, the term "effective amount" means the amount of compound of the instant invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissollution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to treat, inhibit, or prevent the symptoms and/or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg, from one to three times per day. Such dosages will be administered to a patient in need thereof for at least one month, or more typically for six months, or chronically.

The formulations which follow are given for purposes of illustration and are not intended to be limiting in any way. The total active ingredients in such formulations comprises from 0.1% to 99.9% by weight of the formulation. The term "active ingredient" means a compound of formula I.

Formulation 1: Gelatin Capsules

| Ingredient | Quantity (mg/capsule) |
| --- | --- |
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

Formulation 2: Tablets

| Ingredient | Quantity (mg/tablet) |
| --- | --- |
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
| --- | --- |
| Active Ingredient | 0.25 |
| Ethanol | 29.75 |
| Propellant 22 (Chlorodifluoromethane) | 70.00 |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suppositories

| Ingredient | Weight |
| --- | --- |
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension

Suspensions each containing 0.1–1000 mg of a compound of formula I per 5 mL dose.

| Ingredient | Weight |
| --- | --- |
| Active Ingredient | 0.1–1000 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following Examples and Preparations are provided to better elucidate the practice of the instant invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

NMR data for the following Examples were generated on a GE 300 MHz NMR instrument, and anhydrous $CDCl_3$ was used as the solvent unless otherwise indicated. Field strength for $^{13}C$ NMR spectra was 75.5 MHz, unless otherwise indicated.

EXAMPLES

Preparation 1
3,4-dihydro-1-(4-methoxybenzoyl)]-6-methoxy-2-naphthalenyl diphenyl phosphoric acid ester

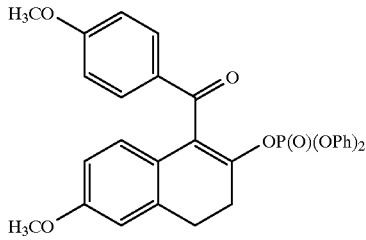

To a solution of 3,4-Dihydro-6-methoxy-1-(4-methoxybenzoyl)-2(1H)-naphthalenone (1.50 g, 0.0048 mol) at 5° C. under $N_2$ in 15 mL $CH_2Cl_2$ was added diphenylchlorophosphate (1.36 g, 0.0051 mol) and 4-dimethylaminopyridine (5 mg). Triethylamine (0.514 g, 0.0051 mol) in $CH_2Cl_2$ (20 mL) as then added dropwise over 10 min, while keeping the reaction temperature below 5° C. The resulting mixture was stirred overnight, and then it was poured over brine and ice and the crude product was extracted by EtOAc (50 mL). The organic layer was washed well with brine, dried over anhydrous $K_2CO_3$, and evaporated to obtain 2.92 g of a yellow oil. Silica gel chromatography which utilized 10% EtOAc in toluene gave the desired product as a yellow oil, 2.17 g (83%) This material gave a strong peak in its field desorption mass spectrum at M/e 542 and was essentially a single component by NMR spectroscopy. Nevertheless, it failed to crystallize and did not give an acceptable combustion analysis for carbon. Anal. ($C_{31}H_{27}PO_7$) calcd C, 68.63; H, 5.02; O, 12.96. Found: C, 65.37; H, 4.89; O, 13.26. $^1$H NMR (CDCl$_3$) δ 7.91 (d, J=8.8 Hz, 2H), 7.20–6.97 (m, 9H), 6.95–6.73 (m, 5H), 6.58 (dd, J=8.5 Hz, J=2.4 Hz, 1H), 3.83 (s, 3H), 3.75 (s, 3H), 3.07 (t, J=7.8 Hz, 2H), 2.88 (t, J=7.8 Hz, 2H); MS (FD) m/e 542 (M+).

Preparation 2
3,4-dihydro-1-[4-[2-(1-piperidinyl)ethoxy]benzoyl)]-6-methoxy-2-naphthalenyl diphenyl phosphoric acid ester

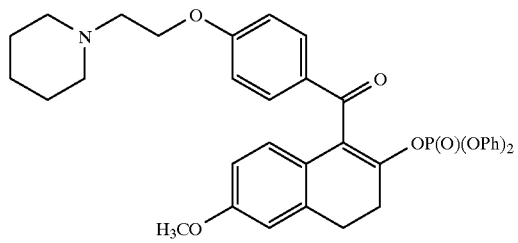

This compound was prepared in an analogous manner to the compound of Preparation 1.

Appearance: dark yellow oil.

$^1$H NMR (CDCl$_3$) δ 7.85 (d, J=8.7 Hz, 2H), 7.39–6.92 (m, 9H), 6.92–6.69 (m, 5H), 6.57 (dd, J=8.5 Hz, J=2.4 Hz, $^1$H), 4.03 (t, J=5.9 Hz, 2H), 3.77 (s, 3H), 3.07 (t, J=8.1 Hz, 2H), 2.89 (t, J=8.1 Hz, 2H),2.78 (t, J=7.2 Hz, 2H), 2.62–2.42 (m, 4H), 1.77–1.55 (m, 4H), 1.55–1.37 (m, 2H); MS (FD) m/e 639 (M+).

Preparation 3
3,4-dihydro-6-methoxy-2-(3-methoxyphenyl)-1-naphthalenyl](4-methoxyphenyl)methanone

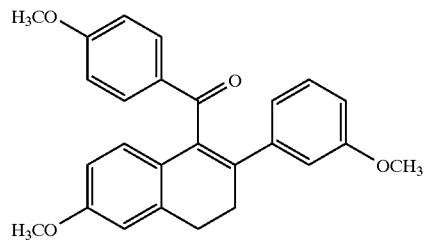

Sodium hydride (60% in mineral oil, 5.4 g, 0.135 mol) was suspended in anhydrous THF (80 mL) under a nitrogen atmosphere and the mixture was cooled to 5° C. in an ice bath. A solution consisting of 3,4-dihydro-6-methoxy-1-(4-methoxybenzoyl)-2(1H)-naphthalenone (38.0 g, 0.122 mol) and diphenyl chlorophosphate (36.3 g, 28.0 mL, 0.135 mol) in THF (150 mL) was added at a rate so that the temperature of the reaction mixture remained below 10° C. Following the initially rapid evolution of hydrogen gas, the reaction mixture was stirred for 2 hr with continued cooling from the ice bath. Analysis of a small sample by TLC (SiO$_2$, Toluene-EtOAc 9:1) showed essentially quantitative formation of the enolphosphate intermediate The reaction mixture was maintained near 0° C. and 3-methoxyphenyl magnesium bromide (250 mL of a 0.74M solution in THF, 0.185 mol) was added by cannula over approximately 5 min. The resulting mixture was stirred at 0° C. for 2 hour, and then it was allowed to warm to 25° C. overnight. By TLC analysis, loss of enolphosphate had accompanied the formation of a major product which migrated at high Rf. The reaction was worked up by pouring it over a large excess of iced NH$_4$Cl solution, and the crude product was extracted with with ethyl acetate. The organic extracts were washed with brine and dried over anhydrous sodium sulfate. After filtration and removal of the solvents, a brown oil was obtained. The oil was purified by chromatography over silica gel which employed a hexane to chloroform gradient. Pooling and concentration of appropriate fractions gave an amber oil which amounted to 40.3 g (83%): $^1$H NMR (CDCl$_3$) δ 7.85 (d, J=8.6 Hz, 2H)7.10–7.0 (m, 1H), 6.90–6.70 (m, 6H), 6.70–6.60 (m, 2H), 3.80 (s, 6H), 3.67 (s, 3H), 3.10–2.90 (m, 2H), 2.90–2.70 (m, 2H); MS (FD) m/e 400 (M+); Anal. Calc'd. for $C_{26}H_{24}O_4$; C, 77.98; H, 6,04; N, 0.00. Found: C, 77.49; H, 6.20; N, 0.00.

Preparation 4
[3,4-dihydro-6-methoxy-2-(3-methoxyphenyl)-1-naphthalenyl] [4-[2-(1-piperidinyl)ethoxy]phenyl] methanone hydrochloride

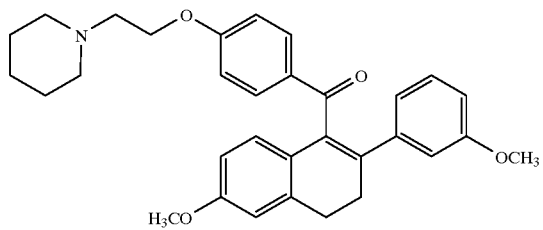

Sodium hydride (60% in mineral oil, 2.68 g, 0.067 mol) was suspended in anhydrous THF (300 mL) under a nitrogen atmosphere and the suspension was cooled to 5° C. in an ice bath. A solution consisting of a compound of Preparation 2 (26.0 g, 0.0638 mol) in a minimum of THF was added dropwise and after the evolution of hydrogen subsided, the mixture was kept cooled and stirred for an hour to complete formation of the enolate. With continued cooling, diphenyl chlorophosphate (17.1 g, 13.2 mL, 0.0638 mol) in THF (75 mL) was added at a rate so that the temperature of the reaction mixture remained below 10° C. Following the completion of the addition, the reaction mixture was allowed to warm to room temperature while stirring was continued. Analysis of a small sample by TLC ($SiO_2$, Toluene EtOAc 9:1) showed essentially quantitative formation of the enol phosphate intermediate. The reaction mixture was maintained near 5° C. and 3-methoxyphenyl magnesium bromide (150 mL of a 0.64M solution in THF, 0.096 mol) was added by cannula. The resulting mixture was stirred at 0° C. for 1 hour, and then it was allowed to warm to 25° C. and stirred for one hour longer. The reaction was kept cooled and carefully quenched by gradual addition of 50 mL of 1N sulfuric acid. After adjusting the pH to 7.0, most of the THF was removed under reduced pressure. The aqueous residue was distributed between water and chloroform. The organic layer was washed with brine and dried over anhydrous sodium sulfate. Concentration provided an oil which was purified by chromatography over silica gel which utilized a gradient of chloroform to 95:5 (chloroform:methanol) to elute the product. Appropriate fractions provided 36 gms of the crude free base, which was dissolved in methanol and treated with an excess of 5N HCl solution, then concentrated to dryness. The residue was recrystallized from methanol-ethyl acetate to provide 27.8 g (82%) of the desired hydrochloride salt: $^1$H NMR (DMSO-$d_6$) δ 10.09 (bs, 1H), 7.76 (d, J=8.7 Hz, 1H), 7.11–7.02 (m, 2H), 6.94 (d, J=8.8 Hz, 1H), 6.86 (d, J=1.2 Hz, 1H), 6.81–6.72 (m, 2H), 6.66 (dd, J=8.2 Hz, 2.5, 1H), 6.61 (d, J=3.1 Hz, 1H), 4.37 (t, J=4.6 Hz, 2H), 3.69 (s, 3H), 3.57 (s, 3H), 3.01–2.82 (m, 4H), 2.78–2.63(m, 2H), 1.81–1.58 (m, 5H), 1.31 (m, 1H); MS (FD) m/e 497 (M+; loss of HCl); Anal. Calc'd. for Anal. Calc'd. for $C_{32}H_{36}ClNO_4$: C, 71.96; H, 6.79; N, 2.62. Found: C, 71.69; H, 6.77; N, 2.48.

Preparation 5
3,4-Dihydro-6-methoxy-2-(3-methoxyphenyl)-1-naphthalenyl](4-hydroxyphenyl)methanone

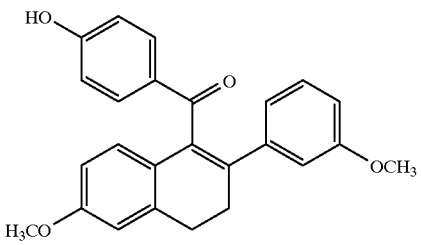

To EtSH (12.5 g, 14.9 mL. 0.20 mol) in anhydrous ethyl ether (300 mL) at −78° C. under a dry nitrogen atmosphere in a 1 L single neck RB flask was added slowly via syringe 1.6M n-BuLi (113 mL, 0.180 mol) over 1 hour. After addition was complete, the ether was removed under vacuum and a solution of 3,4-dihydro-6-methoxy-2-(3-methoxyphenyl)-1-naphthalenyl](4-methoxyphenyl)methanone (24.0 g, 0.065 mol) in anhydrous DMF (150 mL) was added. The reaction mixture was heated at 70–80° C. for 2.5 hours and then at 65° C. for 20 hr. TLC analysis ($SiO_2$, Toluene-EtOAc 9-1) showed the starting material to be nearly gone. Two spots were present at lower $R_f$. These were attributed to the desired product and the corresponding diphenol (lowest spot). The reaction mixture was allowed to cool and was then poured into 500 mL iced 1N HCl solution. The crude product was extracted into EtOAc. The EtOAc phase was washed with saturated aq. NaCl solution, dried over anhydrous $MgSO_4$, and evaporated to a yellow oil. The product was purified by chromatography over silica gel using a gradient consisting of chloroform changing linearly 95:5 chloroform:methanol. Following evaporation of the appropriate fractions, a yellow oil was obtained which was recrystallized from ethyl ether to yield 21.3 g, (54%) of the desired product, mp 197–8° C. $^1$H NMR (CDCl$_3$) δ 7.76 (d, J=8.6 Hz, 2H), 7.10–7.00 (m, 1H), 6.90–6.70 (m, 4H), 6.70–6.60 (m, 4H), 6.07 (bs, 1H), 3.78 (s, 3H), 3.62 (s, 3H), 3.10–2.90 (m, 2H), 2.90–2.70 (m, 21H); MS (FD) m/e 386 (M+); Anal. Calc'd. for $C_{25}H_{22}O_4$: C, 77.70; H, 5.74. Found: C, 77.45; H, 5.66.

Preparation 6

3,4-Dihydro-6-methoxy-2-(3-methoxyphenyl)-1 naphthalenyl] [4-[2-(1-piperidinyl)ethoxy] phenylmethanone

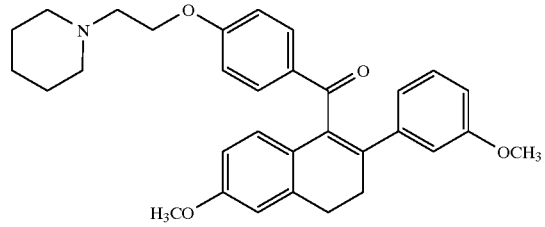

3,4-dihydro-6-methoxy-2-(3-methoxyphenyl)-1-naphthalenyl] (4-hydroxyphenyl)methanone (3.5 g, 9.0 mmol), anhydrous $K_2CO_3$ (6.25 g, 45 mmol), N-2-chloroethyl-piperidine hydrochloride (1.75 g, 9.5 mmol, Aldrich Chem. Co.) 10 mg of KI, and anhydrous DMF (150 mL) were combined under a nitrogen atmosphere and the resulting mixture was stirred at room temperature for 16 hr. The DMF was removed under reduced pressure and the residue was distributed into water and ethyl acetate. The organic layer was separated, washed with brine and dried over anhydrous sodium sulfate. After concentration to an oil, the product was purified by column chromatography over silica gel using a gradient from chloroform to 95:5 chloroform:methanol. The appropriate fractions gave, on evaporation of the solvent and vacuum drying of the residue at 80° C. overnight, an oil which weighed 3.1 g. (69% ). $^1$H NMR (CDCl$_3$) δ 7.80 (d, J=9.0 Hz, 2H), 7.10–7.00 (m, 1H), 6.90–6.70 (m, 6H), 6.70–6.68 (m, 2H), 4.09 (t, J=5.9 Hz, 2H), 3.78 (s, 3H), 3.65 (s, 3H), 3.02 (t, J=8.1 Hz, 2H), 2.90–2.70 (m, 4H), 2.60–2.40 (m, 3H), 1.70–1.50 (m, 5H), 1.50–1.01 (m, 2H); MS (FD) m/e 497 (M+); Anal. Calc'd. for $C_{32}H_{35}NO_4$: C, 77.24; H, 7.09; N, 2.82. Found: C, 77.05; H, 7.19; N, 3.05.

Example 1
4-(3,8-dimethoxy-11H-benzo[a]fluoren-11-yl)phenol

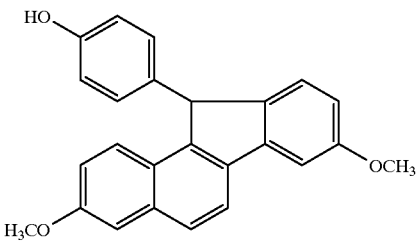

3,4-dihydro-6-methoxy-2-(3-methoxyphenyl)-1-naphthalenyl] (4-methoxyphenyl)methanone (5.0 g, 12.95 mmol) was added to 98% methanesulfonic acid (50 mL) which was stirred vigorously at 25° C. under an atmosphere of nitrogen. The resulting dark reaction mixture was allowed to stir for 15 min and then it was quenched by the addition of ice (300 g). The crude product was then extracted with two 100 mL portions of ethyl acetate. The combined extracts were washed with brine and with saturated sodium bicarbonate solution, dried over anhydrous magnesium sulfate and concentrated. The resulting oily solid was purified by chromatography over silica gel which employed a gradient system that consisted initially of toluene:ethyl acetate 95:5 and changed linearly to 75:25 over 40 minutes at a flow rate of 150 mL/min. The appropriate fractions were combined and concentrated to yield 3.0 g of the desired product as an amorphous solid.

$^1$H NMR (DMSO-$d_6$) δ 9.18 (s, 1H), 8.02 (d, J=8.4 Hz, 1H) 7.85 (d, J=8.5 Hz, 1H), 7.51–7.43 (m, 2H), 7.36 (s, 1H), 7.07 (d, J=8.2 Hz, 1H), 7.00 (dd, J=9.0 Hz, J=2.5 Hz, 1H), 6.79 (d, J=8.4 Hz, 2H), 6.72 (dd, J=8.4 Hz, J=2.3 Hz, 1H), 6.57 (d, J=8.3 Hz, 2H), 5.27 (s, 1H), 3.80 (s, 3H), 3.79 (s, 3H); MS (FD) m/e 368 (M+); Anal. Calc'd. for $C_{25}H_{20}O_3$: C, 81.50; H, 5.47; O, 13.03. Found: C, 81.21; H, 5.63.

Example 2
3,8-Methoxy-11-[4-[2-(1-piperidinyl)ethoxy]phenyl]-11H-benzo[a]fluorene

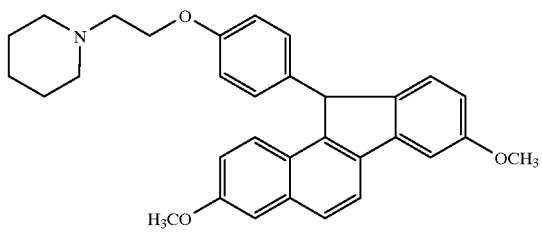

By a procedure analogous to that used in example 1, the hydrochloride salt of the product of Preparation 4 (300 mg) was cyclized using methane sulfonic acid (3 mL). The reaction was allowed to proceed for 15 min. and then quenched by cautious addition of small portions of the reaction mixture to a large excess of iced saturated sodium bicarbonate solution. When effervesence ceased, the product was extracted by two 100 mL portions of ethyl acetate. The combined organic extracts were washed with brine, dried over anhydrous magnesium sulfate, and concentrated to provide the desired product (253 mg, 94%) as a cream colored solid, mp 158–9° C.

$^1$H NMR (DMSO-$d_6$) δ 8.04 (d, J=8.6 Hz, 1H), 7.87 (d, J=8.6 Hz, 1H), 7.51–7.43 (m, 2H), 7.36 (d, J=1.9 Hz, 1H), 7.09–6.94 (m, 2H), 6.90 (d, J=8.3 Hz, 2H), 6.80–6.65 (m, 3H), 5.34 (s, 1H), 3.94 (t, J=5.7 Hz, 2H), 3.81 (s, 3H) 3.79 s, 3H), 2.55 (t, J=5.65 Hz, 2H), 2.40–2.22 (m, 4H) 1.51–1.32 (m, 5H), 1.31–1.22 (m, 1H); (M+); Anal. Calc'd. for $C_{32}H_{33}NO_3$. 0.5 mol $H_2O$: C, 80.14; H, 6.93; N, 2.92. Found: C, 78.66; H, 7.01, N, 2.87.

Example 3
3,8-Dihydroxy-11-[4-[2-(1-piperidinyl) ethoxy]phenyl]-11H-benzo[a]fluorene hydrochloride

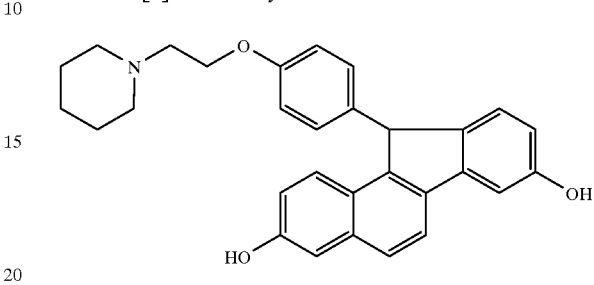

To a solution of [3,4-dihydro-6-methoxy-2-(3-methoxyphenyl)-1-naphthalenyl] [4-[2-(1-piperdinyl)ethoxy]phenylmethanone] hydrochloride (10.00 g, 18.7 mmol) in 500 mL of anhydrous methylene chloride under $N_2$ at 0° C. was added boron tribromide (8.85 mL, 0.00 mmol). The resulting mixture was allowed to stir at 0–5° C. for 5 hours. The reaction was then poured into a stirring solution of cold saturated sodium bicarbonate (large excess). When gas evolution ceased, the aqueous layer was extracted with 5% methanol/chloroform (3×200 mL). The organic layer was combined, dried (sodium sulfate), and concentrated in vacuo to an oil. The oil was purified by chromatography over a silica gel column with THF:methanol 9:1 as the elution solvent. The crude free base which was a greenish solid weighing 8.46 g, was dissolved in 100 mL of methanol, and treated with 4 mL of 5N hydrochloric acid and then concentrated to dryness. the resulting solid was washed with 1:1 chloroform:methanol, collected by filtration. and dried in vacuo. After drying, desired product was obtained (5.5 g (60%) as a white, crystalline solid, mp 183–4° C.

$^1$H NMR (DMSO-$d_6$) δ 9.93 (bs, 1H), 9.70 (s, 1H), 9.36 (s, 1H), 7.85 (d, J=8.3 Hz, 1H), 7.72 (d, J=8.5 Hz, 1H), 7.43 (d, J=8.9 Hz, 1H), 7.18 (d, J=14.2 Hz, 2H), 7.00–6.9 (m, 4H), 6.81 (d, J=8.40 Hz, 2H), 6.56 (d, J=8.4 Hz, 1H), 5.28 (s, 1H), 4.30–4.20 (m, 2H), 3.50–3.30 (m, 4H), 3.00–2.80 (m, 2H), 1.80–1.50 (m, 5H), 1.32 (bs, 1H); MS (FD) m/e 452 (M+); Anal. Calcld. for $C_{30}H_{30}NO_3$: C, 73.84; H, 6.20; N, 2.87. Found: C, 73.46; H, 6.16; N, 2.76.

Example 4
3,8-Dihydroxy-11-[4-[2-(1-piperidinyl)ethoxy]phenyl]-11H-benzo[a]fluorene, hydrochloride

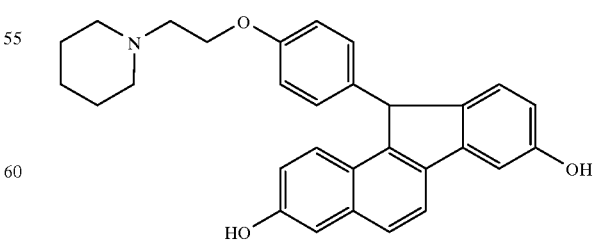

A solution of [3,4-dihydro-6-methoxy-2-(3-methoxyphenyl)-1-naphthalenyl] [4-[2-(1-piperdinyl) ethoxy] phenylmethanone] hydrochloride (8.4 g, 16.9 mmol) in anhydrous methylene chloride (300 mL) was cooled to near 0° C. and treated with. AlCl$_3$ (15.4 g, 118 mmol), followed by ethane thiol (10.4 g, 12.5 mL, 16.9 mmol). The reaction was kept cold and stirred for 30 minutes during which a red precipitate appeared. The addition of additional (80 mL) of ethane thiol dissolved some of the precipitate, and stirring was continued for an additional 2 hours at ice-bath temperature. The reaction mixture was treated with 100 mL of THF, which dissolved much of the now abundant red precipitate. Methanol (200 mL was then added and the red precipitate dissolved completely. The reaction mixture was concentrated to near dryness and the resulting white suspension was poured into excess sodium carbonate and ice. The resulting mixture was extracted with warm chloroform:methanol 85:15, and the extracts were evaporated to dryness. The residue was applied to a pad of silica gel and placed on top of a silica gel column which was eluted with 75:25 ethyl acetate:methanol. Appropriate fractions provided 4.1 grams of crude product for which an attempted purification by recrystallization (from a mixture of methanol, ethyl acetate, and chloroform) was attempted. Eventually a small amount of crystals were isolated as the hydrochloride to provide 0.49 g (6%) of the desired material.

Test Procedures

In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libi tum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection. After a one week acclimation period (therefore, two weeks post-OVX) daily dosing with test compound was initiated. 17α-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine: xylazine (2:1, V:V) mixture and a blood sample was collected by cardiac puncture. The animals were then sacrificed by asphyxiation with CO$_2$, the uterus was removed through a midline incision, and a wet uterine weight was determined.

Cholesterol Analysis. Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotemetrically at 500 nm. Cholesterol concentration was then calculated against a standard curve.

Uterine Eosinophil Peroxidase (EPO) Assay. Uteri were kept at 4° C. until time of enzymatic analysis. The uteri were then homogenized in 50 volumes of 50 mM Tris buffer (pH-8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound: 17α-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17α-ethynyl estradiol (EE$_2$; an orally available form of estrogen), and rats treated with certain compounds of the instant invention. Although EE$_2$ caused a decrease in serum cholesterol when orally administered at 0.1 mg/kg/day, it also exerted a stimulatory action on the uterus so that EE$_2$ uterine weight was substantially greater than the uterine weight of ovariectomized test animals. This uterine response to estrogen is well recognized in the art.

Not only did the compounds of the instant invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the instant invention did not cause any increase in the number of eosinophils observed in the stromal layer of ovariectomized rats, while estradiol cause a substantial, expected increase in eosinophil infiltration.

The data presented in Tables 1 and 2 below reflects the response of 5 to 6 rats per treatment.

4-Day OVX Rat assay:

TABLE 1

| | | Experiment 1 | | |
|---|---|---|---|---|
| Compound | Dose (mg/kg)[a] | Uterine Wt. (% Inc.)[b] | Uterine EPO (Vmax)[c] | Serum Cholesterol (% Dec.)[d] |
| EE$_2$[e] | 0.1 | 200.2* | 276.5* | 98.6* |
| Example 3 | 0.1 | −28.4* | 9.2 | 68.9* |
| | 1 | −14.5* | 13.0 | 67.0* |
| | 10 | −22.2* | 8.8 | 72.1* |

TABLE 2

Experiment 2

| Compound | Dose (mg/kg)[a] | Uterine Wt. (% Inc.)[b] | Uterine EPO (Vmax)[c] | Serum Cholesterol (% Dec.)[d] |
|---|---|---|---|---|
| EE$_2$[e] | 0.1 | 135.0* | 250.1* | 100* |
| Example 3 | 0.01 | 57.6* | 7.6 | 24.5 |
|  | 0.1 | 3.2* | 5.8 | 74.5* |
|  | 1 | 3.5* | 9.0 | 73.6* |

[a]mg/kg PO
[b]Uterine weight % increase versus the ovariectomized controls
[c]Eosinophil peroxidase, V$_{max}$
[d]Serum cholesterol decrease versus ovariectomized controls
[e]17-α-Ethynyl-estradiol In addition to the demonstrated benefits of the compounds of the instant invention, the above data clearly demonstrate that compounds of formula I are not estrogen mimetics. Furthermore, no deleterious toxicological effects (for example, survival numbers) were observed with any treatment.

Osteoporosis Test Procedure

Following the General Preparation Procedure, infra, the rats were treated daily for 35 days (6 rats per treatment group) and sacrificed by carbon dioxide asphyxiation on the 36th day. The 35 day time period was sufficient to allow maximal reduction in bone density, measured as described herein. At the time of sacrifice, the uteri were removed, dissected free of extraneous tissue, and the fluid contents were expelled before determination of wet weight in order to confirm estrogen deficiency associated with complete ovariectomy. Uterine weight is routinely reduced about 75% in response to ovariectomy. The uteri were then placed in 10% neutral buffered formalin to allow for subsequent histological analysis.

The right femurs were excised and digitilized x-rays generated and analyzed by an image analysis program (NIH image) at the distal metaphysis. The proximal aspect of the tibiae from these animals were also scanned by quantitative computed tomography.

In accordance with the above procedures, compounds of the instant invention and ethynyl estradiol (EE$_2$) in 20% hydroxypropyl β-cyclodextrin were orally administered to test animals. Distal femur metaphysis and proximal tibiae data were the results of formula I compound treatments compared to intact and ovariectomized test animals. Results are reported as percent protection relative to ovariectomy, as provided in Table 3 below.

In summary, ovariectomy of the test animals causes a significant reduction in femur density compared to intact, vehicle treated controls. Orally administered ethynyl estradiol (EE$_2$) prevented this loss, but the risk of uterine stimulation with this treatment is ever-present.

TABLE 3

| Compound | Dose mg/kg | Body Weight Change % dec. vs. OVX | Femur x-ray % prot | Tibia BMD % prot |
|---|---|---|---|---|
| EE2 | 0.1 | 109.2 | 32.4 | 60.9 |
| Example 3 | 0.01 | 36.4 | 6.4 | 18 |
|  | 0.1 | 68.8 | 39.9 | 62.8 |
|  | 1.0 | 79.5 | 30.8 | 58.3 |

MCF-7 Proliferation Assay

MCF-7 breast adenocarcinoma cells (ATCC HTB 22) were maintained in MEM (minimal essential medium, phenol red-free, Sigma, St. Louis, Mo.) supplimented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) (maintenance medium). Ten days prior to assay, MCF-7 cells were switched to maintenance medium supplemented with 10% dextran coated charcoal stripped fetal bovine serum (DCC-FBS) assay medium) in place of 10% FBS to deplete internal stores of steroids. MCF-7 cells were removed from maintenance flasks using cell dissociation medium (Ca$^{++}$/Mg$^{++}$ free HBSS (phenol red-free) supplemented with 10 mM HEPES and 2 mM EDTA). Cells were washed twice with assay medium and adjusted to 80,000 cells/mL. Approximately 100 mL (8,000 cells) were added to flat-bottom microculture wells (Costar 3596) and incubated at 37° C. in a 5% CO$_2$ humidified incubator for 48 hours to allow for cell adherence and equilibration after transfer. Serial dilutions of drugs or DMSO as a diluent control were prepared in assay medium and 50 mL transferred to triplicate microcultures followed by 50 mL assay medium for a final volume of 200 mL. After an additional 48 hours at 37° C. in a 5% CO$_2$ humidified incubator, microcultures were pulsed with tritiated thymidine (1 uCi/well) for 4 hours. Cultures were terminated by freezing at −70° C. for 24 hours followed by thawing and harvesting of microcultures using a Skatron Semiautomatic Cell Harvester. Samples were counted by liquid scintillation using a Wallace BetaPlace β counter. The compounds of formula I are active and potent in inhibiting the tumor cell growth, for example, the compound of Example 3 has an IC$_{50}$ of 0.11 nM.

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenzo[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements

I claim:

1. A compound of formula I

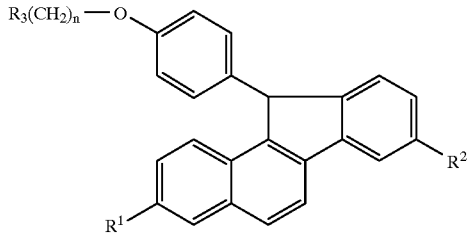

wherein:
- $R^1$ is —H, —OH, —O($C_1$-$C_4$ alkyl), —OCO($C_1$-$C_6$ alkyl), —O(CO)O($C_{1-C6}$ alkyl), —OCOAr, —O(CO)OAr, where Ar is phenyl or optionally substituted phenyl, or —OSO$_2$($C_2$-$C_6$ alkyl);
- $R^2$ is —OH, —O($C_1$-$C_4$ alkyl), —OCO($C_1$-$C_6$ alkyl), —O(CO)O($C_{1-C6}$ alkyl), —OCOAr, —O(CO)OAr, where Ar is phenyl or optionally substituted phenyl, or —OSO$_2$($C_2$-$C_6$ alkyl);
- $R^3$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino; and
- n is 2 or 3; with the proviso that at least one of $R^1$ and $R^2$ must be —OCO($C_1C_6$-alkyl), —O(CO)O($C_1$-$C_6$ alkyl), —OCOAr, —O(CO)OAr, or —OSO$_2$($C_2$-$C_6$ alkvl); or a pharmaceutically acceptable salt or solvate thereof.

2. A compound according to claim 1 wherein n is 2.

3. A compound according to claim 2 wherein $R^3$ is 1-piperidinyl.

4. A compound according to claim 3 wherein said salt thereof is the hydrochloride salt.

5. A pharmaceutical formulation comprising a compound according to claim 1 in combination with a pharmaceutically acceptable carrier, diluent, or excipient.

6. A method of inhibiting bone loss or bone resorption which comprises administering to a patient in need thereof an effective amount of a compound of claim 1.

7. A method according to claim 6, wherein said bone loss or bone resorption is due to menopause or ovariectomy.

8. A method of lowering serum cholesterol levels which comprises administering to a patient in need thereof an effective amount of a compound of claim 1.

9. A method of inhibiting estrogen-dependent cancer which comprises administering to a patient in need thereof an effective amount of a compound of claim 1.

10. A method according to claim 9 wherein said estrogen-dependent cancer is breast cancer.

11. A method according to 9 wherein said estrogen-dependent cancer is uterine cancer.

* * * * *